(12) United States Patent
Misawa et al.

(10) Patent No.: US 7,824,761 B2
(45) Date of Patent: Nov. 2, 2010

(54) METAL STRUCTURE AND PRODUCTION METHOD THEREFOR

(75) Inventors: Hiroaki Misawa, Sapporo (JP); Kosei Ueno, Sapporo (JP); Yasuyuki Tsuboi, Sapporo (JP); Keiji Sasaki, Sapporo (JP)

(73) Assignee: National University Corporation Hokkaido University, Sapporo-shi (JP)

( * ) Notice: Subject to any disclaimer, the term of this patent is extended or adjusted under 35 U.S.C. 154(b) by 11 days.

(21) Appl. No.: 11/884,614

(22) PCT Filed: Feb. 16, 2006

(86) PCT No.: PCT/JP2006/302765

§ 371 (c)(1),
(2), (4) Date: Aug. 17, 2007

(87) PCT Pub. No.: WO2006/092963

PCT Pub. Date: Sep. 8, 2006

(65) Prior Publication Data

US 2008/0160287 A1    Jul. 3, 2008

(30) Foreign Application Priority Data

Feb. 17, 2005    (JP) .............................. 2005-040227

(51) Int. Cl.
*B32B 9/00* (2006.01)
(52) U.S. Cl. ..................................... 428/209
(58) Field of Classification Search .................. 428/209
See application file for complete search history.

(56) References Cited

FOREIGN PATENT DOCUMENTS

| | | |
|---|---|---|
| JP | 2003-315531 | 12/2003 |
| JP | 2004-292627 | 10/2004 |

OTHER PUBLICATIONS

Linden S. et al., Controlling the Interaction between Light and Gold Nanoparticles: Selective Suppression of Extinction, Physical Review Letters, Voi.86, No. 20, pp. 4688 to 4691, May 14, 2001.*
JP 2000-173978 Translation of abstract and Description.*
Craighead, H.G, et al., "Characterization and optical properties of arrays of small gold particles", *App. Phys. Lett.* vol. 44, pp. 1134-1136, (Jun. 15, 1984).
Gotschy, W., et al., "Thin films by regular patterns of metal nanoparticles: tailoring the optical properties by nanodesign", *App. Phys.* B63, pp. 381-384, (1996).

* cited by examiner

*Primary Examiner*—Keith D Hendricks
*Assistant Examiner*—Daniel Miller
(74) *Attorney, Agent, or Firm*—The Nath Law Group; Jerald L. Meyer; Robert T. Burns

(57) ABSTRACT

A metal structure capable of significantly increasing wavelength selectivity and polarization electivity for an incident light, and a production method thereof. First, a solid transparent substrate (glass substrate) (10) is cleaned and dried (S100). The surface of the substrate (10) is spin-coated with a positive electron lithography-use resist solution and then baked, and the resist solution is removed to form a resist thin film (20) on the substrate (10) (S200). A specified pattern is drawn on the resist thin film (20) with an electron beam, and the film is developed, rinsed and dried (S300). Then, metals such as chromium and then gold are formed sequentially on the substrate (10) by sputtering (S400). And, excessive resist materials are removed from the surface of the substrate (10) (S500), whereby metal nano-rod array (40) is completed. The metal nano-rod array (40) has a structure in which many metal nano-rods having their sizes precisely controlled are integrated on the substrate (10) at constant fine intervals and with their directions aligned in one axial direction.

4 Claims, 8 Drawing Sheets

RESIST COATING

ELECTRON BEAM
LITHOGRAPHING
/ DEVELOPING

METAL FILM FORMING

LIFTING-OFF
/ RESIST SEPARATING (240+x) nm
120 nm

METAL STRUCTURE AND PRODUCTION METHOD THEREFOR

TECHNICAL FIELD

The present invention relates to a metal structure and a manufacturing method thereof. More particularly, the present invention relates to a metal structure that can control plasmon resonance absorption wavelengths and a manufacturing method thereof.

BACKGROUND ART

A fine metal, for example, a fine metal having a surface structure on a nanometer scale and a metallic fine particle of a nanometer size shows a characteristic optical response (optical absorption) called "localized (surface) plasmon resonance absorption" in a specific wavelength range according to its shape and size. Examples of metal showing the localized plasmon resonance absorption include noble metals such as gold, silver and platinum, but it is important that, even if the same kind of metal is used, plasmon resonance absorption wavelengths are different depending on the size and shape. Making full use of such properties, the application to various kinds of optical devices (for example, optical filters) of fine metal or metallic fine particles described above is expected.

The localized plasmon resonance absorption also includes an important application. Intensity of the optical response (light emission or Raman scattering) of molecules adsorbed onto a metal showing plasmon resonance is significantly increased ($10^4$ times or more) by an interaction between the molecules and surface plasmon. That is, a metal structure having a fine metal showing plasmon resonance prepared on a substrate will function as a high sensitivity sensor device for a molecular system, and research and development of application to this field is actively conducted.

When a metal structure having a substrate on which a plurality of metallic fine particles having plasmon resonance absorption are arranged is applied to various kinds of optical devices or high sensitivity sensors, first, it is important to control a position of plasmon resonance absorption wavelengths and polarization selectivity of incident light to be absorbed. Characteristics of a plasmon resonance absorption band (such as resonance absorption wavelengths, spectral line shapes and polarization selectivity) are sensitive to orderliness of the size and shape of each metallic fine particle, and also sensitive to orderliness of the distance between metallic fine particles arranged on the substrate, distribution (variability) of the distance and directional properties of arrangement. Therefore, a nanostructure of metallic fine particles and arrangement of a plurality of metallic fine particles on the substrate must be precisely controlled in order to control optical response characteristics of the surface plasmon. If the metallic fine particles are rod-shaped metallic fine particles (metallic nano-rods), the shape thereof can be specified by, for example, the aspect ratio (ratio of the major axis length and minor axis length).

For example, Patent Document 1 discloses an optical filter consisting of an acrylic resin film with thickness of several μm into which gold nano-rods is distributed, the rods having an anisotropic shape whose average length of minor axis is 10 nm and that of major axis is 100 nm or less. In this case, the aspect ratio of the gold nano-rod is 10 or less. It has been confirmed that an optical filter prepared in this way has light transmittance of 15 percent or less in all wavelength ranges of 800 nm to 1000 nm and 1200 nm to 1600 nm due to plasmon resonance of gold nano-rods and thus operates as an excellent optical filter in the near-infrared region.

Furthermore, according to Patent Document 2, resin material containing gold nano-rods (composition containing gold nano-rods) having a small variation coefficient (20 percent or less) of major axis and minor axis lengths (that is, sizes of the gold nano-rods are roughly the same), prepared through a reduction of metallic ion shows relatively sharp wavelength characteristics of plasmon absorption (that is, wavelength selectivity is high).

Patent Document 1: Japanese Patent Application Laid-Open No. 2003-315531

Patent Document 2: Japanese Patent Application Laid-Open No. 2004-292627

DISCLOSURE OF INVENTION

Problems to be Solved by the Invention

However, in the invention disclosed in Patent Document 1, the optical filter can operate as an optical filter in a wide wavelength range, but, in other words, this means wavelength selectivity is low. "Wavelength selectivity" means a property that selectively absorbs a specific range of wavelengths while allowing other ranges of wavelengths to transmit. Degradation of such wavelength selectivity is mainly caused by unevenness (variability) in size of fine metals (gold nano-rods). Variability of the distance between metallic fine particles also causes a big problem, but Patent Document 1 refers to nothing on this point.

Patent Document 1 also discloses an optical filter having absorption maxima near 900 nm and 700 nm using the film into which "gold nano-rods whose average length of minor axis is 10 nm and whose average length of major axis is 50 nm" and "gold nano-rods whose average length of minor axis is 10 nm and whose average length of major axis is 30 nm" are distributed, respectively, that is, an optical filter having wavelength selectivity, but does not disclose any specific absorption spectrum.

The invention disclosed in Patent Document 2 is intended to overcome the problem of insufficient wavelength selectivity of the invention disclosed in Patent Document 1, but still remains the following problem.

In development of optical devices and high sensitivity sensors using resonance plasmon absorption, it is preferable that, in addition to the wavelength selectivity as described above, resonance plasmon absorption also has selectivity regarding polarization, which is another important characteristic of light. That is, if a response from a metal structure device including fine metal showing resonance plasmon absorption is different depending on the direction of light incident on the metal structure device, the optical response function and sensor function of the device will be greatly expanded.

However, a composition containing gold nano-rods disclosed in Patent Document 2 does not have such polarization selectivity at all. This is mainly because, though variability in size of the gold nano-rods is small, the "orientation (direction)" of the gold nano-rods having an anisotropic shape is completely random in the composition and thus is not identical.

Also, when the polarization selectivity is low, optical response wavelength characteristics (absorption spectrum) obtained after adding all polarization responses will be broader, causing, as a result, a problem of low wavelength selectivity as well.

In the techniques disclosed in Patent Documents 1 and 2, as described above, there is a problem of a degraded or lacking function of wavelength selectivity and polarization selectivity for incident light in an optical response of fine metal having resonance plasmon absorption.

The present invention has been made in view of the above circumstances and an object thereof is to provide a metal structure that can enormously improve wavelength selectivity and polarization selectivity for incident light and a manufacturing method thereof.

Means for Solving the Problem

A metal structure according to the present invention shows plasmon resonance absorption and adopts a configuration including a plurality of rod-shaped metallic fine particles that have a constant size and are arranged on a substrate at a constant interval in a fixed direction.

The metal structure according to the present invention shows plasmon resonance absorption and includes a plurality of rod-shaped metallic fine particles that have a constant size and are arranged on a substrate at a constant interval in a fixed direction.

Also, a metal structure according to the present invention shows plasmon resonance absorption and adopts a configuration including a substrate and a plurality of rod-shaped metallic fine particles with a constant volume arranged on the substrate, wherein: each of the metallic fine particles has a constant major axis length and a constant minor axis length when viewed from a top surface perpendicular to the substrate; each of the metallic fine particles has a shortest distance to mutually adjacent metallic fine particles shorter than a predetermined value; and at least one of the major axis and the minor axis of the metallic fine particles is aligned in the same direction.

Also, a metal structure manufacturing method according to the present invention for manufacturing the metal structure, includes: a step of forming a resist thin film on a substrate; a step of forming a predetermined pattern on the resist thin film formed on the substrate; a step of forming a metal film on the substrate where the predetermined pattern is formed on the resist thin film; and a step of removing an excessive resist film from the substrate where the metal film is formed.

Advantageous Effect of the Invention

According to the present invention, it is possible to substantially improve wavelength selectivity and polarization selectivity for incident light of a metal structure having plasmon resonance absorption.

BEST MODE FOR CARRYING OUT THE INVENTION

Figure 1:
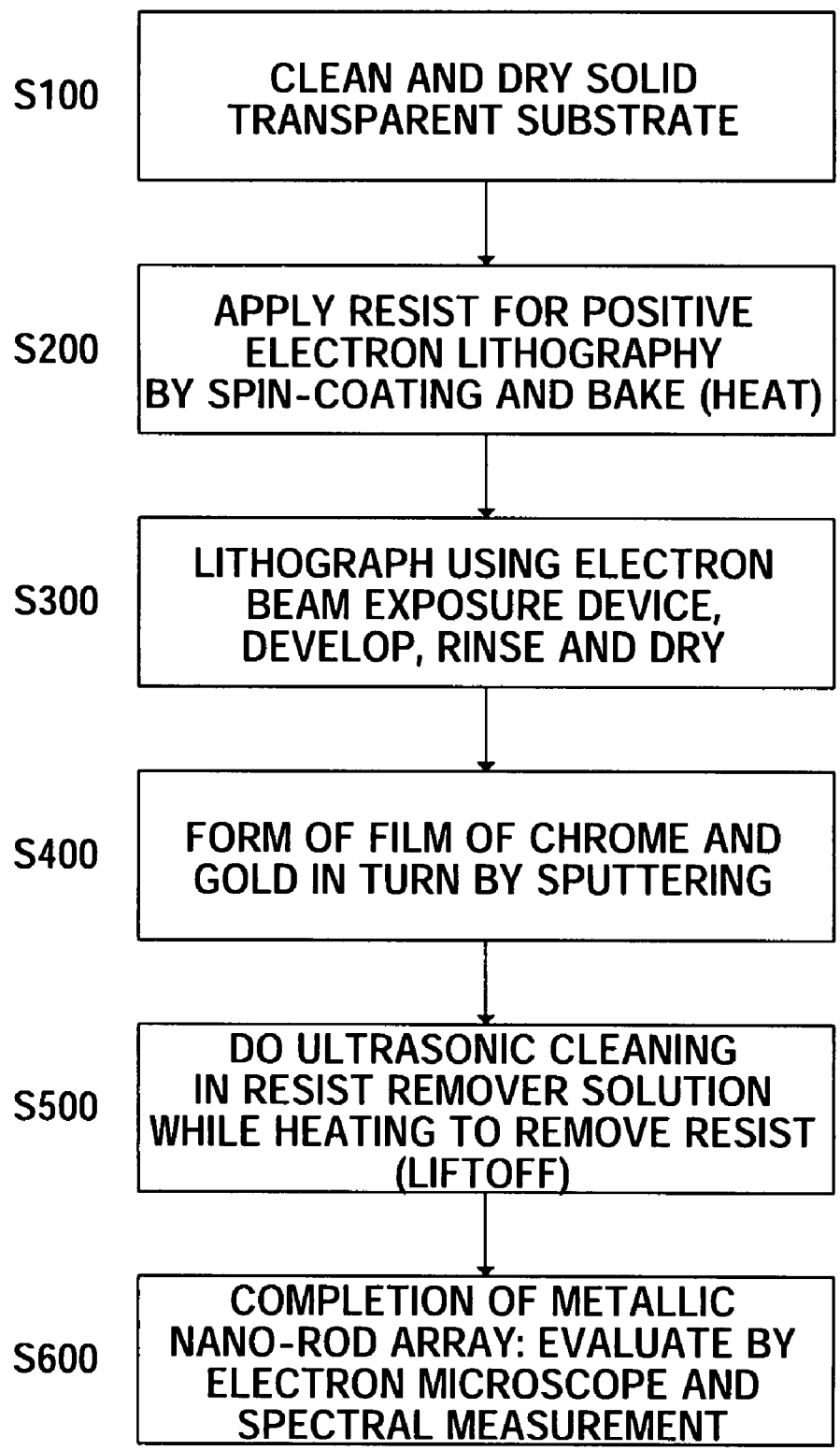
FIG. 1 is a flowchart showing steps of a manufacturing method of a metal structure according to an embodiment of the present invention.

The present inventors have found that, in order to improve wavelength selectivity and polarization selectivity for incident light, it is necessary to align each of the size and shape of metallic fine particles, directional properties of arrangement of metallic fine particles and distance (interval) between metallic fine particles in a metal structure. The inventors also have found that, in order to align each of the size and shape of metallic fine particles, directional properties of arrangement of metallic fine particles and distance (interval) between metallic fine particles, it is necessary to arrange metallic fine particles precisely and regularly on a substrate by applying semiconductor microfabrication technique.

The present invention assembles a metal structure device in which many rod-shaped metallic fine particles (for example, metallic nano-rods) each size of which is precisely controlled are integrated on a solid substrate such as glass at a constant microscopic interval and each direction of which is aligned in an axis direction by applying semiconductor microfabrication technique. Thus, a metal structure having excellent wavelength selectivity and extremely sensitive polarization selectivity for incident light in plasmon resonance absorption characteristics can be prepared.

Characteristics of a metal structure of the present invention, that is, characteristics of the material, shape, size, interval and direction of a plurality of metallic fine particles formed on a substrate will be specifically described below.

(Material of Metallic Fine Particles)

As described above, metallic fine particles in the present invention are metallic fine particles having plasmon resonance absorption. Metals having plasmon resonance absorption include, for example, noble metals such as gold, silver, copper and platinum. Metallic fine particle may be made of another material plated with these noble metals.

The substrate included in a metal structure of the present invention and on which metallic fine particles having the plasmon resonance absorption are arranged is not particularly limited, but a substrate of solid material having no light absorption in the range of the visible region to the near-infrared region is preferable in order to make the metal structure operate as an optical response device. Specific examples of solid material include glass, quartz and sapphire.

(Shape of Metallic Fine Particles)

As described above, metallic fine particles in the present invention have a rod shape. Each metallic fine particle only needs to be a fine particle showing plasmon resonance, but for example, the size (volume equivalent diameter) thereof is preferably 1-1000 nm, and more preferably 10-500 nm. "Rod shape" means a shape of hexahedron whose adjacent surfaces are all mutually orthogonal. If rod-shaped metallic fine particles are viewed from a top surface perpendicular to the substrate, the rod-shaped metallic fine particles preferably look like rectangular particles. Each vertex of a rectangle need not necessarily look like a true right angle, and, for example, may show a round shape or a shape whose vertex edge is trimmed. However, in this case, it is preferable that each vertex of a rectangle has a uniform shape. In the following, it is assumed that the aspect ratio of rod-shaped metallic fine particles means an aspect ratio obtained by the ratio of the major axis and minor axis of the rectangular metallic fine particles.

(Sizes of Metallic Fine Particles)

As described above, metallic fine particles in the present invention have a constant size. "Constant size" means that, when rod-shaped metallic fine particles arranged on a substrate are viewed from a top surface perpendicular to the substrate, the major axis and minor axis each have a constant length and each metallic fine particle has a constant area and a constant volume. "The area of a rod-shaped metallic fine particle" specified here means an area of a rectangular rod-shaped metallic fine particle when the rod-shaped metallic fine particle is viewed from a top surface perpendicular to the substrate.

"The major axis and minor axis each have a constant length" means, variability in length of at least one of the major axis and minor axis, preferably both axis, of a plurality of rod-shaped metallic fine particles is 5 percent or less.

Here, if the major axis and minor axis each have a constant length when a plurality of rod-shaped metallic fine particles are viewed from a top surface perpendicular to the substrate, the rectangular area of each of the metallic fine particles when these metallic fine particles are viewed from the top surface perpendicular to the substrate will also be constant.

"The area is constant" means that variability in the area of metallic fine particles is 5 percent or less, preferably 2 percent or less. "The volume is constant" means that variability in the volume of metallic fine particles is 5 percent or less, preferably 3 percent or less.

More specifically, the area of a rod-shaped metallic fine particle is preferably 100 nm$^2$ to 30000 nm$^2$ and the volume of a rod-shaped metallic fine particle is preferably 1000 nm$^3$ to 3000000 nm$^3$. The height (thickness) of a rod-shaped metallic fine particle from the substrate can be derived from the area and volume of the rod-shaped metallic fine particle and is preferably 300 nm or less, more preferably 100 nm or less.

The area and volume of each metallic fine particle when viewed from a top surface perpendicular to the substrate can be confirmed and calculated from metallic fine particles taken in an electron microscope photo. For example, the major axis length and minor axis length of a rod-shaped metallic fine particle are read from an electron microscope photo viewing the rod-shaped metallic fine particle from a top surface perpendicular to the substrate, and both are multiplied to calculate the area of the metallic fine particle. Also, the height of the rod-shaped metallic fine particle is read from an electron microscope photo viewing the rod-shaped metallic fine particle from a side parallel to the substrate and the calculated area and the read height are multiplied to calculate the volume of the metallic fine particle.

(Interval of Metallic Fine Particles)

As described above, metallic fine particles in the present invention are arranged at constant intervals. "The interval is constant" means that the shortest distance between any one metallic fine particle among a plurality of metallic fine particles arranged on a substrate and an adjacent metallic fine particle is 200 nm or less (preferably 100 nm or less) and its variability is 5 percent or less.

Here, variability in the major axis length and minor axis length of a rod-shaped metallic fine particle and that in the interval between metallic fine particles can be confirmed and calculated by measuring and analyzing plasmon resonance absorption spectrum of a prepared metal structure. That is, a nano-scale processing resolution and variability in each parameter of metallic fine particles can be calculated by irradiating a rod-shaped metal structure with incident light having polarization in a predetermined direction and comparing wavelength positions of absorptions maxima of obtained plasmon resonance absorption spectra.

In the present invention, wavelength selectivity of a metal structure can be improved by fixing the shape and size of each metallic fine particle, and interval of metallic fine particles, in the metal structure.

(Direction of Metallic Fine Particles)

As described above, metallic fine particles in the present invention are arranged in a fixed direction. "Fixed direction" means that at least one of the major axis and minor axis of rod-shaped metallic fine particles is aligned in the same direction.

In the present invention, polarization selectivity of a metal structure can be improved by fixing the shape and size of each metallic fine particle in the metal structure and arranging each metallic fine particle in a fixed direction.

Here, polarization selectivity of a metal structure means that, for incident light having two polarization directions mutually orthogonal on a plane perpendicular to the incident light, two maxima of plasmon resonance absorption spectra corresponding to the two polarization directions are caused for plasmon resonance. That is, an orientation of metallic fine particles so as to cause two absorption maxima in major axis and minor axis directions of a rod-shaped metal structure is obtained.

In order to realize high sensitivity sensing, a difference between the two maxima of plasmon resonance absorption spectra is preferably 50 nm or more, more preferably 100 nm or more.

In summary, wavelength selectivity of a metal structure is improved by fixing the shape and size of each metallic fine particle and interval of metallic fine particles in the metal structure, and polarization selectivity of a metal structure is improved by fixing the shape and size of the metal structure and arranging each metallic fine particle in a fixed direction.

The inventors have found that polarization selectivity of a metal structure greatly depends also on the aspect ratio of rod-shaped metallic fine particles. This is based on findings that the two absorption maxima can be said in other words to be two absorption maxima in the major axis and minor axis directions of the rod-shaped metal structure.

For example, by changing the aspect ratio of rod-shaped metallic fine particle in the range of 1 to 9, each of the two maxima of plasmon resonance absorption spectra corresponding to the two polarization directions can be changed in the range of 500 nm to 1500 nm.

The ratio (aspect ratio) of the major axis and the minor axis of a rod-shaped metal structure is preferably more than 1 and 10 or less, more preferably 3 or more and 7 or less. This is because, if the aspect ratio approaches 1, anisotropy of the shape of each metallic fine particle is reduced or eliminated, leading to insufficient polarization selectivity. And if, on the other hand, the aspect ratio exceeds 10, a maximum wavelength of plasmon resonance absorption spectrum reaches the infrared region, causing a problem that high sensitivity detectors that can detect such a maximum wavelength are limited. Moreover, when plasmon resonance of a metal structure having a maximum wavelength in the infrared region is excited, there also arises a problem that an appropriate laser light source is not easily available.

That is, polarization selectivity of a metal structure of the present invention can be adjusted also by adjusting the aspect ratio of rod-shaped metallic fine particle. As described above, "selective polarization" means that, for incident light having two polarization directions mutually orthogonal on a plane perpendicular to the incident light, two peaks (maximum absorption) of plasmon resonance absorption spectra corresponding to the two polarization directions are caused, and a difference between wavelength positions of absorption spectrum maxima can be adjusted by adjusting the aspect ratio. As described above, the difference between wavelength positions of maxima is preferably at least 50 nm or more, more preferably 100 nm or more.

Moreover, as described above, each major axis of rod-shaped metallic fine particles is aligned in parallel with the substrate, and a surface with the largest area of surfaces of rod-shaped metallic fine particles is preferably arranged in contact with the substrate. That is, among three patterns for arranging rod-shaped metallic fine particle in contact with the substrate, it is preferable to arrange rod-shaped metallic fine particle so that the height of metallic fine particle is the lowest. Accordingly, when a metal structure is made to function as an optical response device by irradiating a substrate with light from a direction perpendicular to the substrate, the shape when viewed from above the substrate is anisotropic, that is, rectangular or elliptic instead of being square or circular, and therefore it is possible to obtain the advantage of improving polarization selectivity. It is also possible to obtain the advantage of being easier to produce metallic fine particle, the plasmon resonance absorption wavelength being in the visible region, and metallic fine particle being harder to break, when the height of metallic fine particle is lower.

"Metal structure" in this specification means an assembly of metal (metallic fine particles) such as a metallic nano-rod array and is used in a context to include a metal structure device, which is a substrate on which an assembly of metal (metallic fine particles) is arranged. That is, a metal structure of the present invention could include a plurality of metallic fine particles and a substrate on which the plurality of metallic fine particles are arranged. By appropriately selecting the substrate, metal structures of the present invention can be used as various kinds of optical devices. By selecting a solid transparent substrate as the substrate, for example, a metal structure of the present invention can be used as an optical filter.

The embodiment of the present invention will further be described below with reference to drawings. In the following description, a case will be described as an example where metallic fine particles are metallic nano-rods.

FIG. 1 is a flowchart showing steps of a manufacturing method of a metal structure according to the embodiment of the present, invention. FIG. 2A to FIG. 2E are sectional views by process for illustrating the manufacturing method in FIG. 1.

Figure 2A:
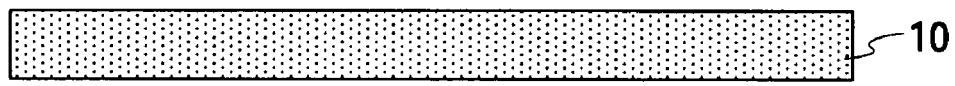
FIG. 2 shows sectional views by process for illustrating the manufacturing method in FIG. 1.

First, in step S100 (process 1), solid transparent substrate 10 (for example, a glass substrate) is cleaned and dried sufficiently (see FIG. 2A). This is because if the surface of substrate 10 is not made sufficiently clean, metallic nano-rods to be prepared on substrate 10 in a later process could be peeled off from substrate 10.

Figure 2B:
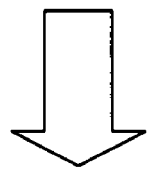
Figure 2B:
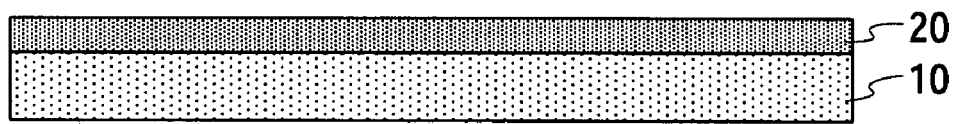

Then, in step S200 (process 2), after spin-coat (rotating) application of a resist solution for positive electron lithography to the cleaned surface of substrate 10, the coated resist is baked (heated) and the resist solvent is removed to form resist thin film 20 on substrate 10 (see FIG. 2B).

At this point, in order to realize finer metallic nano-rods to be formed in a later process, resist thin film 20 formed on substrate 10 preferably has thickness of 1 μm or less, and more specifically, preferably 200 nm or less. The inventors have found that, in order to form such a thin resist film, a resist solution obtained by diluting a commercial resist with a dedicated solvent by a dilution factor of about 2 may be used for spin-coat application.

Here, a reason for making the thickness of resist thin film 20, 200 nm or less in order to realize finer metallic nano-rods is as follows. When the thickness of resist film 20 is 200 nm or more, the overall thickness of thick resist film must be exposed to an electron beam when the electron beam is used for lithographing/exposure, and thus an acceleration voltage of the electron beam must be extremely high. A spatial resolution of lithographing can in general be made finer with an increasing acceleration voltage of the electron beam, but with such an extremely high acceleration voltage, the spatial resolution of lithographing is contrarily lowered. Thus, in order to achieve a spatial resolution for precisely lithographing a metallic nano-rod structure of the size desired in the present invention, the acceleration voltage need not be extremely high and the thickness of 200 nm or less becomes suitable for the acceleration voltage necessary in this case.

Then, in step S300 (process 3), a predetermined pattern is drawn on resist thin film 20 formed in step S200 (process 2) using, for example, an electron beam exposure device (not shown). Here, the predetermined pattern is a trace of an integration arrangement diagram of a desired metallic nano-rod array.

At this point, in order to achieve formation of predetermined fine metallic nano-rods (lengths both in the major axis direction and minor axis direction are 100 nm or less) in a later process, optimization of exposure conditions for the electron beam exposure process becomes extremely important. The inventors have found optimization conditions shown below after repeatedly performing detailed experiments. As optimization conditions for exposure, it is preferable to increase the acceleration voltage of an electron beam and at the same time, to substantially reduce a dose rate of exposure. More specifically, when, for example, the acceleration voltage of an electron beam is 100 kV to 200 kV and the dose rate of exposure is 2 μC/cm² or less, fine metal could be formed on a substrate. Deserving special mention is an extremely low dose rate condition and, for example, as a guide, the dose rate of 1 μC/cm² corresponds to ¹⁄₁₀₀ of the dose rate recommended for the used resist.

Here, a reason why the acceleration voltage of an electron beam is increased and the dose rate of exposure is substantially reduced as the optimization conditions for exposure is as follows. As described above, the spatial resolution of processing (lithographing) can be improved by increasing the acceleration voltage of an electron beam. This is because the speed of the electron beam increases with a higher acceleration voltage, making the de Broglie wavelength of electrons shorter. On the other hand, increasing dose rate of exposure corresponds to making an exposure time longer. A longer exposure time makes it impossible to ignore vibration of a specimen (for example, air-conditioning noise in a laboratory and extremely fine vibration noise of a device) during exposure, causing "blurriness" at processed form ends and leading to lower processing resolution.

Figure 2C:
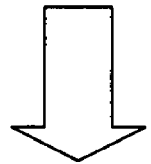
Figure 2C:
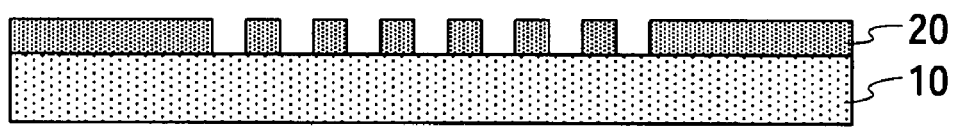

Further, in step S300 (process 3), resist thin film 20 on which exposure/lithography by an electron beam has been performed are developed, rinsed and dried (see FIG. 2C). The development time is also an important parameter in the present manufacturing method and the development time is preferably longer than a standard time corresponding to the lower dose rate, and, more specifically, the development time is preferably, approximately 30 minutes, for example.

Figure 2D:
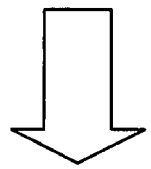
Figure 2D:
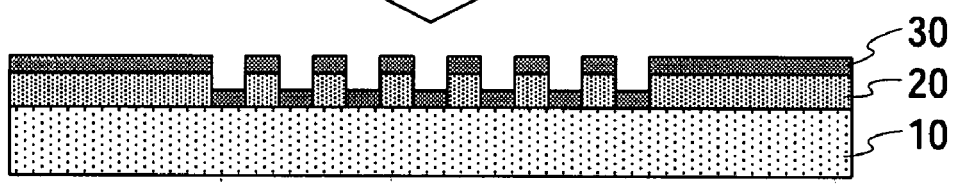

Then, in step S400 (process 4), a film of chrome, then that of metal such as gold are formed by sputtering in turn on substrate 10 processed in step S300 (process 3) (See FIG. 2D). The chrome layer is about 2 nm thick and is used to enhance adhesiveness between solid transparent substrate 10 and metal layer such as gold. Metal such as gold is a material showing a plasmon resonance response in the present invention and its thickness in film formation is 10 nm to 100 nm. This thickness corresponds to that of metallic nano-rods to be prepared. Reference numeral 30 in FIG. 2D indicates a metal film (the chrome layer and a layer of metal such as gold) formed by sputtering.

Figure 2E:
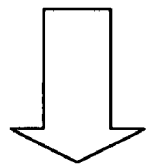
Figure 2E:
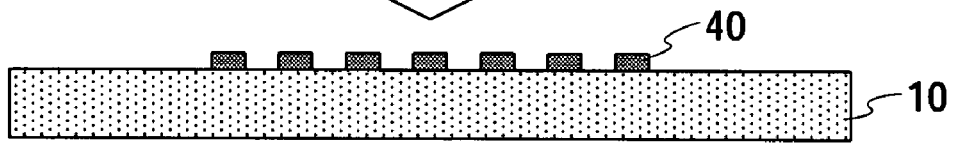

Then, in step S500 (process 5), as the last step of preparing a metallic nano-rod array, excessive resist material is removed (peeled off) from substrate 10 processed in step S400 (process 4) (see FIG. 2E). Removal of resist in this process is called "liftoff." In the liftoff, for example, substrate 10 processed in step S400 (process 4) is soaked in a chemical solution called a resist remover to perform ultrasonic cleaning to remove excessive resist. Metallic nano-rod array 40 is thereby completed.

At this point, according to experiment, excessive resist is not completely removed even after performing ultrasonic cleaning at ordinary temperature (room temperature). The inventors succeeded in completely removing excessive resist by performing ultrasonic cleaning while heating up to 65 degrees to 70 degrees. That is, the inventors have found that in addition to ultrasonic cleaning, heating is needed in the liftoff process.

Here, a reason for performing heating in the present process in addition to ultrasonic cleaning is as follows. If the resist material to be used is polymer, the resist (polymer) is softened by raising the temperature close to a glass transition temperature or the resist (polymer) is made more solvable by DMF (dymethylformamide), which is a solvent for solving the polymer.

Then, in step S600 (process 6), metallic nano-rod array 40 completed in step S500 (process 5) is evaluated by an electron microscope and optical measurement. More specifically, the fine structure of the completed metallic nano-rod array is clarified by the electron microscope, and further the plasmon resonance absorption response with respect to the completed metallic nano-rod array is evaluated by measuring polarization absorption spectrum using an optical microscope.

Results of actual evaluation in step S600 (process 6) will be summarized. Structurally, according to the manufacturing method of a metal structure of the present invention, the sizes (the lengths of the major axis and minor axis, area and volume of each metallic fine particle when viewed from a top surface perpendicular to the substrate) of a prepared metallic nano-rod array can be controlled precisely on a nanometer scale. Moreover, size variability of each can be suppressed to 5 percent or less. Also, the shortest distance between adjacent metallic nano-rods in the prepared metallic nano-rod array can be reduced to 100 nm or less and its variability can be suppressed to 5 percent or less. Further, the major axis or minor axis of each metallic nano-rod can be arranged along one axis direction, that is, the major axis direction or minor axis direction of each metallic nano-rod can be arranged to be in parallel with each other. Such designs (size, shape, directional properties and interval) can be arbitrarily prepared by patterning of electron beam exposure lithographing.

Here, how to calculate variability in the major axis length and minor axis length of a rod-shaped metallic fine particle and that in the interval between metallic fine particles will be described. Variability (processing resolution) in each parameter of metallic fine particle is generally evaluated by directly observing prepared metallic fine particle using an electron microscope, but evaluating the variability with a resolution of several nanometers is difficult.

Thus, calculation of variability with a resolution of several nanometers is performed by measuring and analyzing plasmon resonance absorption spectrum of a prepared metal structure. That is, a nano-scale processing resolution can be realized by irradiating a rod-shaped metal structure with incident light having polarization in a predetermined direction and comparing wavelength positions of absorption maxima of obtained plasmon resonance absorption spectra, and variability in each parameter of metallic fine particles can be calculated. A more specific description will be given below using FIG. 3.

Figure 3A:
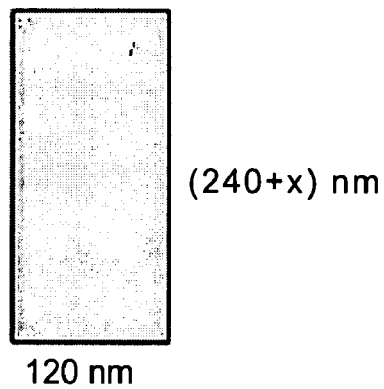
FIG. 3 shows an example of a calculation method of processing resolution of metallic fine particles using plasmon resonance absorption spectra.
Figure 3B:
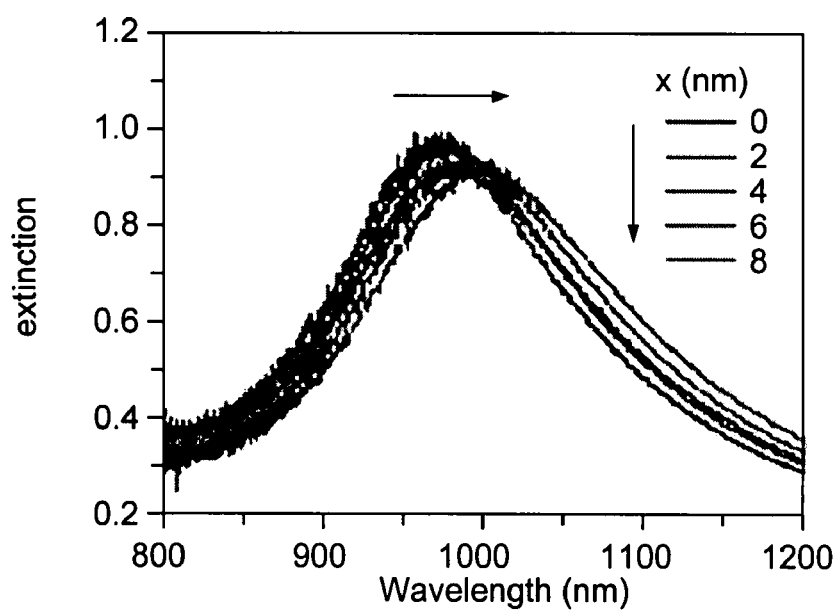
Figure 3C:
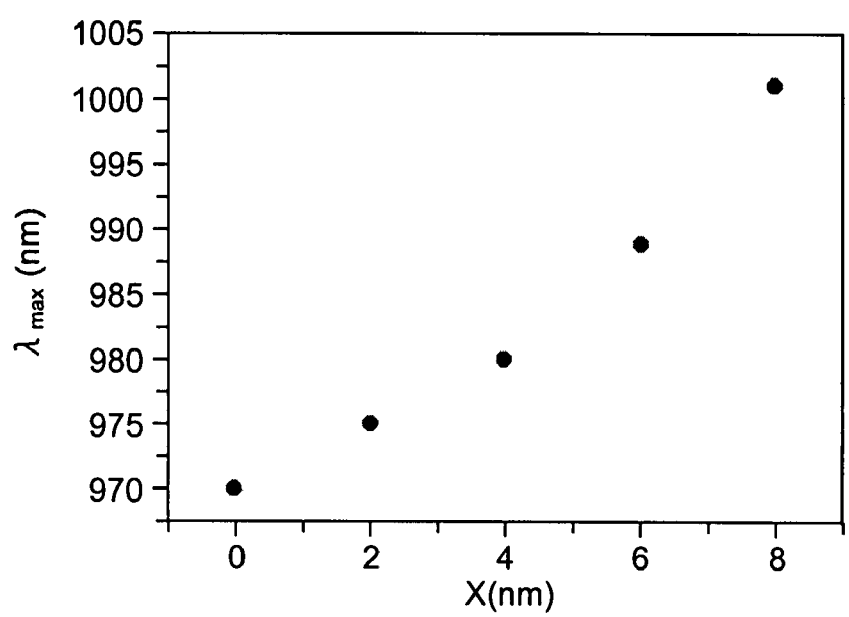

Optical characteristics of a rectangular solid metallic fine particle designed by standardizing the length in the minor axis direction at 120 nm and the height at 60 nm and changing the length in the major axis direction to 240, 242, 244, 246 and 248 nm are as shown in FIG. 3B and FIG. 3C. Here, the length in the major axis direction of the metallic fine particle can be represented by 240+x (nm) and in which x is an integer satisfying $0 \leq 2x \leq 8$.

FIG. 3B shows plasmon absorption spectra obtained by irradiating rod-shaped metallic fine particles whose major axis length is changed with incident light having polarization in parallel with the major axis direction. With an increasing length in the major axis direction of metallic fine particles, maximum wavelength of plasmon resonance absorption spectrum of metallic fine particles shifts to a longer wavelength side. The maximum wavelengths of plasmon resonance absorption spectra are extremely sensitive to the size (in this case, the length in the major axis direction) of metallic fine particles. Therefore, from the maximum wavelengths of plasmon resonance absorption spectra, in this case, the length in the major axis direction of metallic fine particles, that is, the processing resolution in the major axis direction can be evaluated.

This can also be confirmed from FIG. 3C in which maximum wavelengths of plasmon resonance absorption spectra are plotted with respect to the major axis length of the structure. That is, the size of metallic fine particles can actually be designed and processed with a 2 nm processing resolution. FIG. 3A to FIG. 3C show that variability in various parameters of metallic fine particles can be controlled with a processing resolution of at least 2 nm or less.

The processing resolution of metallic fine particles can be evaluated in various ways by changing the polarization direction of incident light incident on the metallic fine particles. For example, the processing resolution in the minor axis direction can be evaluated from plasmon absorption spectrum obtained by irradiation of incident light having polarization in parallel with the minor axis direction.

The processing resolution in portions where metallic fine particles are arranged and that in portions where no metallic fine particle is arranged can also be evaluated in the same way, so that it is possible to calculate and control variability in the interval between metallic fine particles.

A metallic nano-rod array prepared by the above manufacturing method can have a function (wavelength selectivity of optical responses) having plasmon resonance absorption characteristics (absorption wavelength position) highly dependent on the aspect ratio of metallic nano-rods and also a function of generating three-dimensionally uniform polarization from incident light. Also, the metallic nano-rod array can have a function (polarization selectivity of optical responses) by which plasmon resonance absorption is vastly different between incident light having polarization in parallel with the major axis direction with respect to metallic nano-rods and that having polarization in parallel with the minor axis direction. That is, two polarization directions mutually orthogonal with respect to incident light exist, and two absorption maxima are caused in the metallic nano-rod array.

According to the present embodiment, as described above, a metallic nano-rod array is prepared by aligning/integrating a large number of metallic nano-rods whose size hardly varies on a solid transparent substrate with the distance between metallic nano-rods made uniform on a nanometer scale and metallic nano-rod direction arranged in one direction. As a result of that it is possible to prepare a metal structure with an ideal shape/structure that shows resonance plasmon optical response characteristics having excellent wavelength selectivity and high polarization selectivity.

EXAMPLES

A more specific embodiment (example) of the present invention will be described below. However, the present invention should not limitedly be interpreted by the following example.

In the present example, metallic nano-rod arrays are prepared on a glass substrate (Matsunami Glass: 24 mm×24 mm) by electron beam lithography/liftoff. More specifically, after performing ultrasonic cleaning on the glass substrate using acetone, methanol and ultrapure water in this order, the glass substrate is spin-coated (initial: 1000 rpm for 10 seconds, main coating: 4000 rpm for 90 seconds) with a resist for a positive electron lithography (ZEP-520A manufactured by ZEON Corporation, diluted with a special thinner by a factor of 2) and pre-baked on a hot-plate at 180° C. for 3 minutes. Then, after lithographing a predetermined pattern at the dose rate of 1.2 $\mu C/cm^2$ by an electron beam exposure device at the acceleration voltage of 100 kV, the pattern is developed for 30 minutes. Next, after forming a film of 2 nm chrome and 10 nm to 100 nm gold by sputtering on the developed/rinsed substrate, liftoff is performed in a resist remover (dymethylformamide) solution. At this point, clean metallic nano-rod arrays with no residual resist are successfully prepared by applying supersonic waves for 5 minutes while heating the resist remover up to 65 degrees to 70 degrees.

The prepared metallic nano-rods have the length in the major axis direction, length in the minor axis direction, and thickness each in the range of several tens nm to 1000 nm and the distance between metallic nano-rods is designed on a nanometer scale. In this way, various kinds of gold nano-rod arrays with different lengths in major/minor axis directions, thickness, aspect ratio of gold nano-rods and distance between adjacent gold nano-rods (the shortest distance) are prepared.

When two kinds of variability in size of the prepared metallic nano-rods and interval of the prepared metallic nano-rods are measured, variability in the size is 4 percent and that in the interval between metallic nano-rods is 2 percent.

Here, a reason for designing the sizes (the length in the major axis direction, that in the minor axis direction and thickness) of metallic nano-rods on a scale of 1000 nm or less is as follows. If the size of a metal structure is over 1000 nm, the decay time and plasmon resonance absorption wavelength will be shorter in the plasmon resonance for incident light and plasmon resonance energy will be smaller. And therefore, the Q value (resonance sharpness) of plasmon resonance will be smaller. As a result, maxima of plasmon resonance absorption spectra will be broader, making observation of maxima of plasmon resonance absorption spectra more difficult and thus a function as plasmon resonance can be resolved.

Figure 4B:
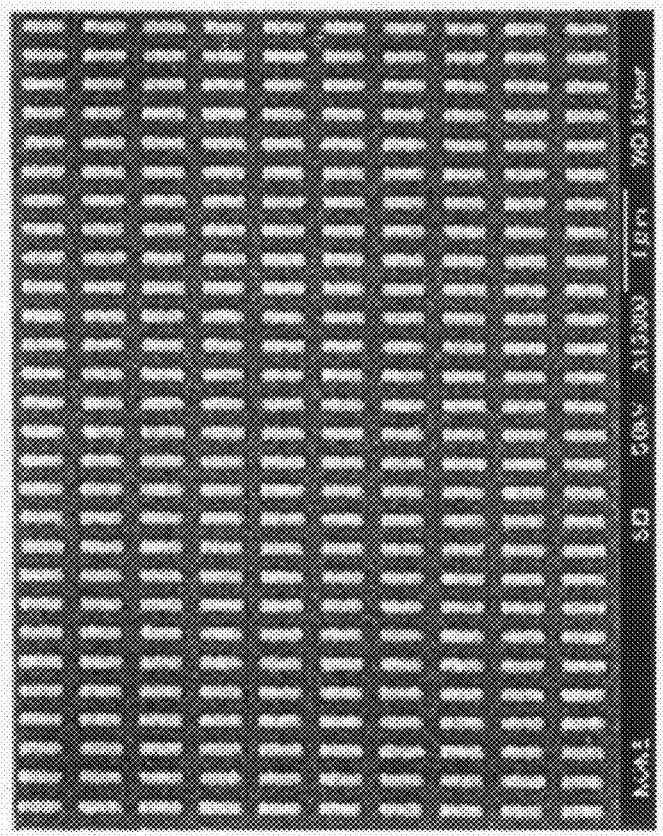
FIG. 4 shows electron microscope photos of actually prepared typical gold nano-rod arrays.
Figure 4A:
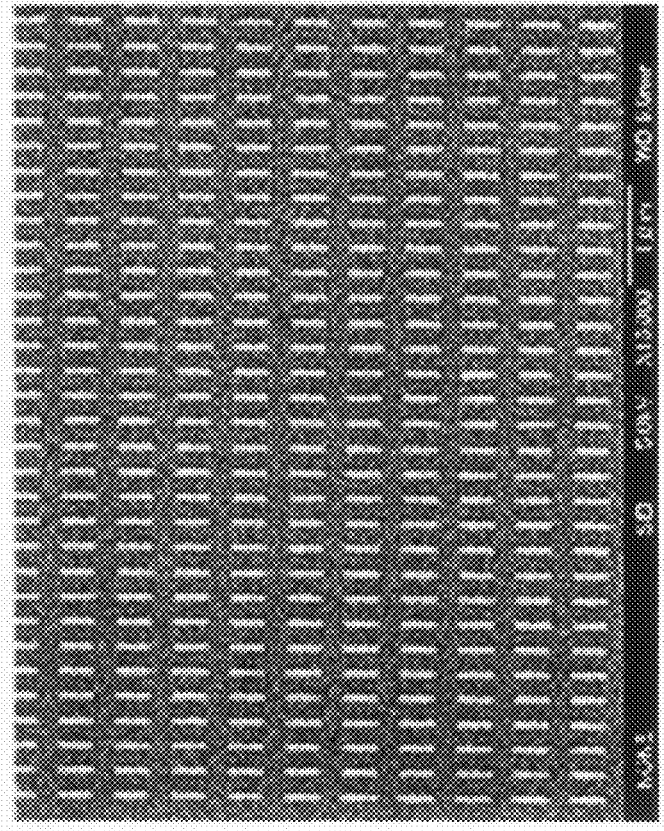

FIG. 4A and FIG. 4B are electron microscope photos of actually prepared typical gold nano-rod arrays. FIG. 4A shows a gold nano-rod array in which the thickness is 60 nm and the lengths in the major axis/minor axis directions are 360 nm×40 nm, and FIG. 4B shows a gold nano-rod array in which the thickness is similarly 60 nm and the lengths in the major axis/minor axis directions are 400 nm×80 nm. According to these figures, the gold nano-rods are prepared and integrated in good order, and it is demonstrated that excellent gold nano-rod arrays can be provided by the present invention.

The inventors performed a detailed evaluation of optical responses of gold nano-rod arrays prepared by the above process. Particularly, experiments were performed by focusing on a correlation between plasmon resonance absorption characteristics and the aspect ratio of gold nano-rods.

Figure 5:
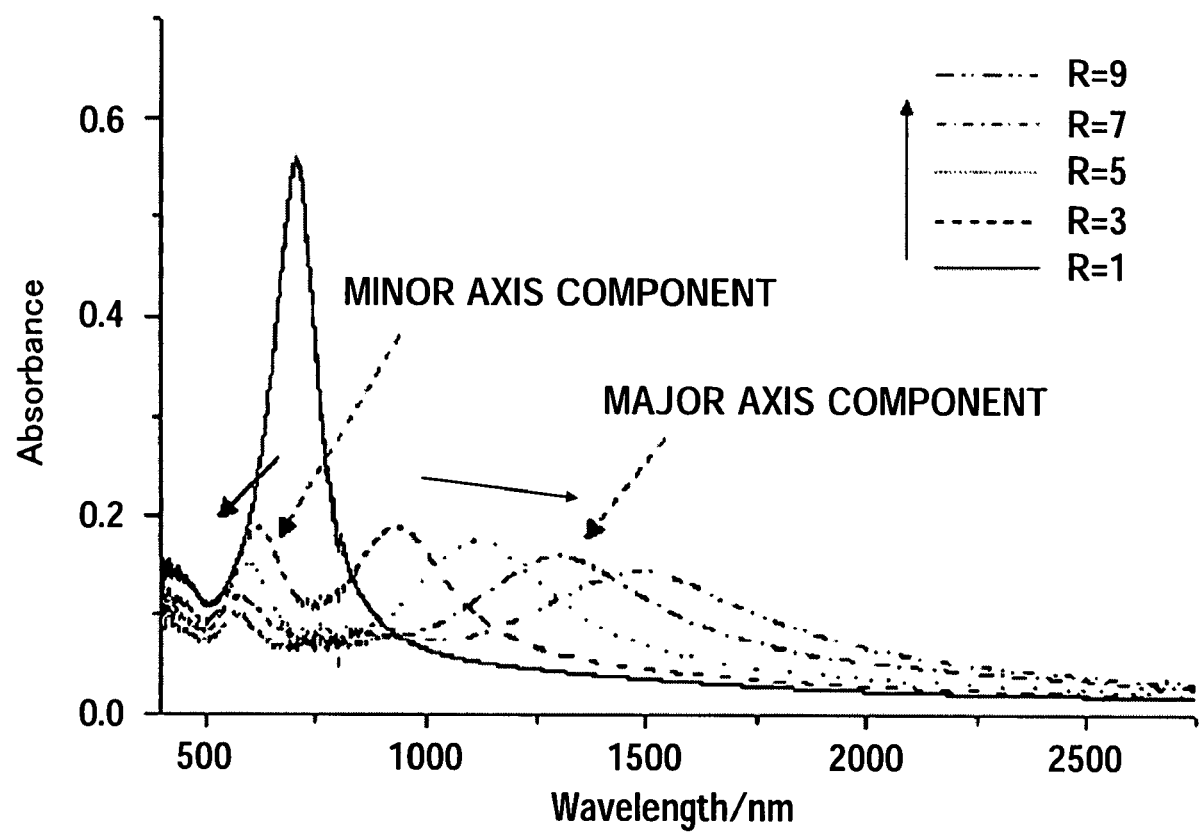
FIG. 5 shows absorption spectra of gold nano-rods measured using non-polarized incident light.
Figure 6:
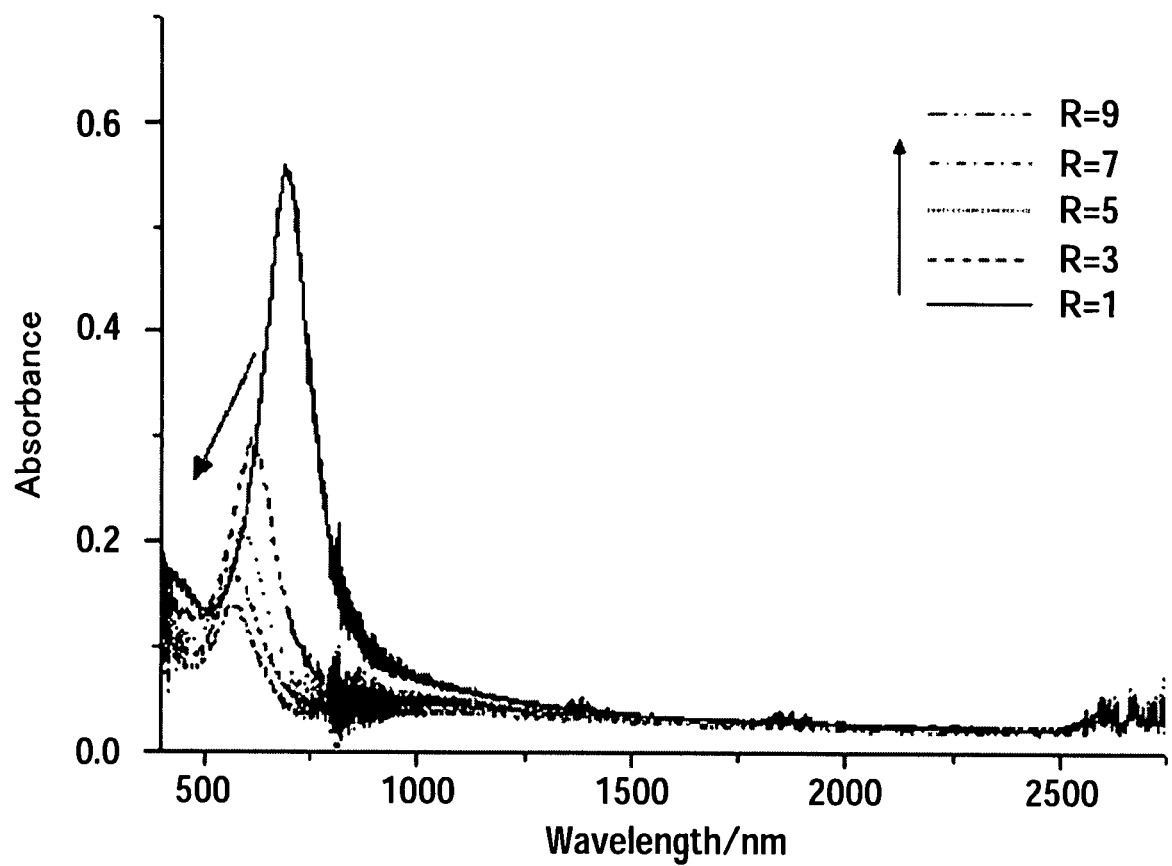
FIG. 6 shows absorption spectra (minor axis component spectra) measured using incident light having polarization in parallel with a minor axis direction of gold nano-rods.
Figure 7:
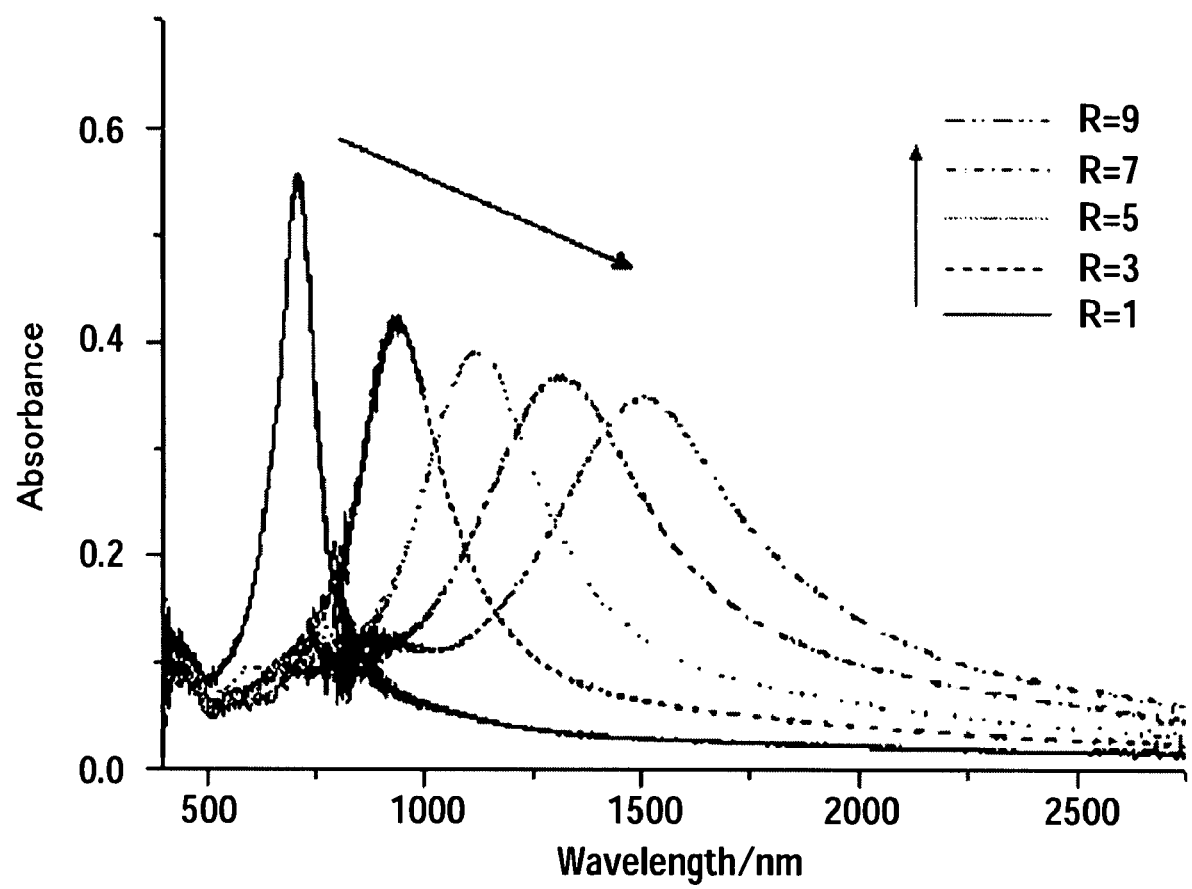
FIG. 7 shows absorption spectra (major axis component spectra) measured using incident light having polarization in parallel with a major axis direction of gold nano-rods.

FIG. 5 to FIG. 7 show plasmon resonance absorption spectra of a gold nano-rod array (gold nano-rod array shown in FIG. 4A) formed by integrating gold nano-rods each having the thickness of 60 nm. These figures show the dependence of the absorption on the aspect ratio (R in these figures) in terms of polarization of incident light. Here, the aspect ratio 1 (R=1) indicates a shape whose length in the major axis direction and that in the minor axis direction are the same, and the shape of a gold nano-rod becomes elongated with an increasing aspect ratio.

FIG. 5 shows absorption spectra of gold nano-rods measured using non-polarized incident light. In this case, broad plasmon absorption bands are observed in a wide wavelength range (500 nm to 2500 nm) from the visible region to the near-infrared region. And two absorption maxima, one in the visible region (500 nm to 700 nm) and the other in the near-infrared region (800 nm to 2500 nm), are observed in FIG. 5.

On the other hand, FIG. 6 shows absorption spectra (minor axis component spectra) measured using incident light having polarization in parallel with the minor axis direction of gold nano-rods, and FIG. 7 shows absorption spectra (major axis component spectra) measured using incident light having polarization in parallel with the major axis direction of gold nano-rods. As is evident from FIG. 6 and FIG. 7, plasmon resonance absorption spectra are entirely different between minor axis components (FIG. 6) and major axis components (FIG. 7). That is, two plasmon resonance absorption maxima which are mutually orthogonal occur in the minor axis direction and major axis direction. Moreover, in each spectrum, the absorption maximum wavelength shifts to the longer wavelength side with an increasing aspect ratio of gold nano-rods.

That is, FIG. 5 to FIG. 7 show that gold nano-rod arrays obtained according to the present invention show, as expected, an optical response (plasmon resonance absorption) having high polarization selectivity and having high wavelength selectivity in spectrum (spectral sensitivity) of each of minor/major axis components. Moreover, non-polarized absorption spectra in FIG. 5 can be interpreted as an addition of minor axis component spectra (FIG. 6) and major axis component spectra (FIG. 7). Conversely, gold nano-rod arrays obtained according to the present invention can be considered to have a function of separating spectral components of minor axis and major axis from non-polarized spectrum and observing such spectral components.

Such behavior is highly interesting and is expected to present valuable findings for device application/design. Thus, the inventors further investigated in detail the dependence of plasmon resonance absorption wavelengths on the aspect ratio.

Figure 8:
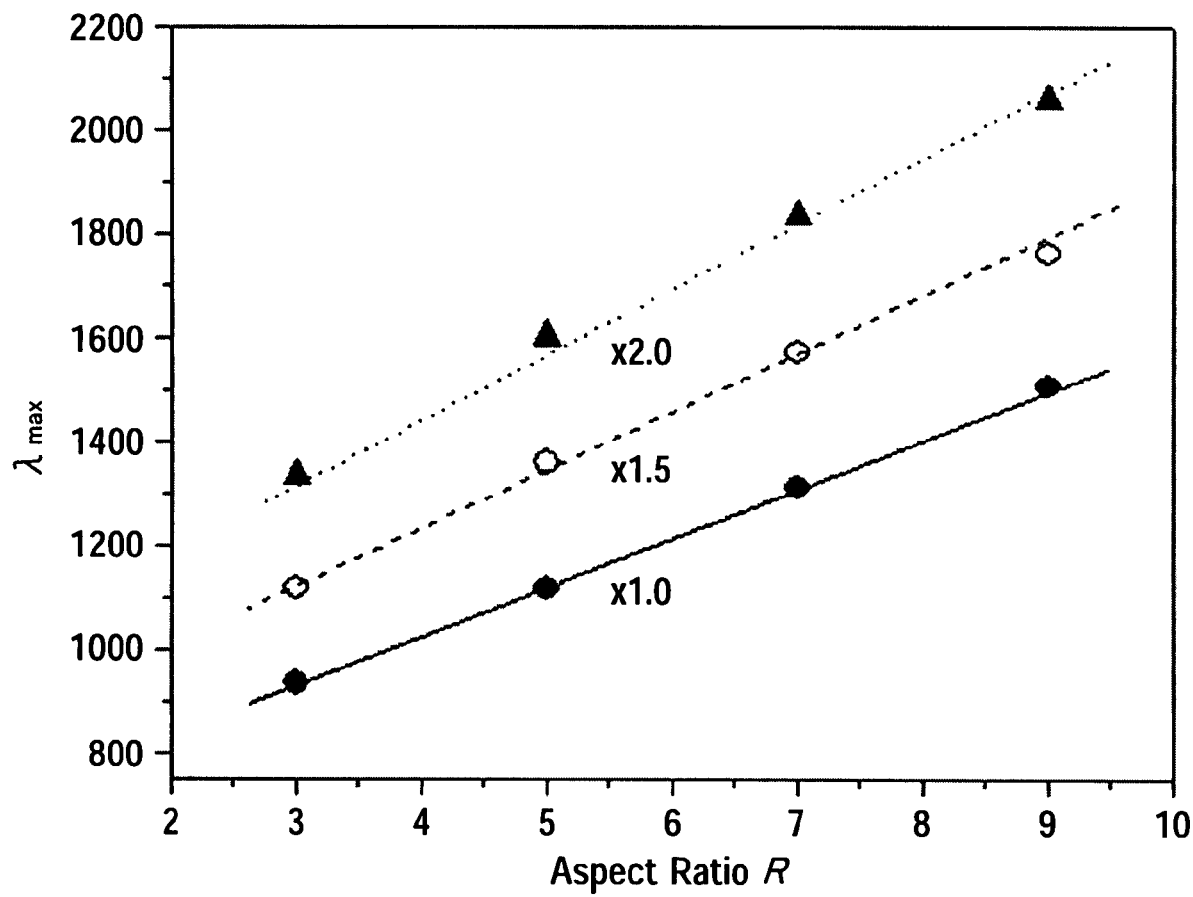
FIG. 8 shows aspect ratio dependence of plasmon resonance absorption wavelengths (major axis direction components) in a gold nano-rod array including gold nano-rods whose length (size) in major axis/minor axis directions is changed while maintaining thickness of the gold nano-rods constant at 60 nm.

FIG. 8 shows the dependence of plasmon resonance absorption wavelengths (major axis direction components) on the aspect ratio in a gold nano-rod array including gold nano-rods whose length (size) in major/minor axis directions is changed while maintaining thickness of the gold nano-rods constant at 60 nm. In FIG. 8, "×1.0" shows a result of plotting data in FIG. 7, and "×1.5" and "×2.0" show results of similar measurements after increasing the size of gold nano-rods by 1.5 times and 2 times, respectively.

What is first evident from these results is that the plasmon resonance absorption position ($\lambda_{max}$) gradually shifts to the longer wavelength side in accordance with an increase in the size of gold nano-rods, ×1.0, ×1.5 and ×2.0. Then, it is striking that there is the linear relation between the plasmon resonance absorption position ($\lambda_{max}$) and the aspect ratio (R). These optical properties can be explained to some extent by a theory showing optical properties of a disperse system of fine particles derived based on the Maxwell-Garnet equation by Gustav Mie in 1908. The present example clearly and experimentally shows that the plasmon resonance absorption position can be precisely controlled by optionally designing the size and shape (aspect ratio) of metallic nano-rods.

Though gold nano-rod arrays are prepared and evaluated in the present example, the nano-rod in the present invention is not limited to gold. The present invention is a highly versatile technique and can provide a fine integrated structure of not only gold, but also silver and platinum. Moreover, its shape is not limited to the rod shape (cylindrical or rectangular solid), and fine integrated structures of various shapes of, for example, disk and nanowires can also be provided.

The present invention provides, as described above, a metal structure having excellent wavelength selectivity and polarization selectivity useful for development of a fine metal structure having a plasmon optical response function, which is an important technique in current optical device development and high sensitivity sensor development, and a manufacturing method thereof.

The present application is based on Japanese Patent Application No. 2005-040227, filed on Feb. 17, 2005, the entire content of which is expressly incorporated by reference herein.

INDUSTRIAL APPLICABILITY

A metal structure according to the present invention and a manufacturing method thereof are useful as a metal structure with plasmon resonance absorption that can enormously improve wavelength selectivity and polarization selectivity for incident light and a manufacturing method thereof. Particularly, a metal structure according to the present invention that can control plasmon resonance absorption wavelengths is useful as an element technology for developing various kinds of optical devices and high sensitivity biosensors.

The invention claimed is:

1. A metal structure showing plasmon resonance absorption, comprising:
    a substrate and a plurality of rod-shaped metallic fine particles on a nanometer scale arranged directly on a surface of the substrate at a constant interval in a fixed direction, the substrate surface being made of transparent insulating material, wherein:
    variability in a major axis length or minor axis length of the plurality of rod-shaped metallic fine particles is 5 percent or less;
    when each of the plurality of rod-shaped metallic fine particles is viewed from a top surface perpendicular to the substrate, an aspect ratio specified by a ratio of a major axis and a minor axis of the rod-shaped metallic fine particles is in the range of 3 to 10;
    two absorption maxima of plasmon resonance absorption spectra corresponding to two polarization directions for incident light having the two polarization directions mutually orthogonal on a plane perpendicular to the incident light are caused;
    a difference between the two absorption maxima of plasmon resonance absorption spectra is in the range of 50 nm to 1000 nm; and
    each of the two absorption maxima of plasmon resonance absorption spectra are variable within the range of 500 nm to 1500 nm.

2. The metal structure according to claim 1, wherein an interval between the mutually adjacent rod-shaped metallic fine particles is 200 nm or less and variability in the interval is 5 percent or less.

3. The metal structure according to claim 1, wherein at least one of a major axis and a minor axis of each of the plurality of rod-shaped metallic fine particles is aligned in a same direction.

4. The metal structure according to claim 1, wherein a major axis of each of the plurality of rod-shaped metallic fine particles is aligned in parallel with the substrate and a surface among surfaces of the plurality of rod-shaped metallic fine particles with a largest area is arranged in contact with the substrate.

* * * * *